United States Patent
Parekh et al.

(10) Patent No.: US 7,014,843 B2
(45) Date of Patent: *Mar. 21, 2006

(54) ENHANCED EFFICACY BASIC ALUMINUM HALIDES/METAL CATION SALT, ANTIPERSPIRANTS ACTIVES AND COMPOSITIONS CONTAINING SUCH MATERIALS AND METHODS FOR MAKING

(75) Inventors: Jawahar C. Parekh, Livingston, NJ (US); Pradip Amin, Edison, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 284 days.

This patent is subject to a terminal disclaimer.

(21) Appl. No.: 10/807,872

(22) Filed: Mar. 24, 2004

(65) Prior Publication Data

US 2005/0214234 A1 Sep. 29, 2005

(51) Int. Cl.
A61K 7/32 (2006.01)
A61K 7/34 (2006.01)
A61K 7/38 (2006.01)
A61K 7/00 (2006.01)

(52) U.S. Cl. .............................. 424/65; 424/66; 424/68; 424/400; 424/401

(58) Field of Classification Search ................... 424/65, 424/66, 68, 400, 401
See application file for complete search history.

(56) References Cited

U.S. PATENT DOCUMENTS

| | | | |
|---|---|---|---|
| 3,981,986 A | 9/1976 | Rubino | |
| 4,017,599 A | 4/1977 | Rubino | |
| 4,028,390 A | 6/1977 | Rubino | |
| 4,223,010 A | 9/1980 | Rubino | |
| 5,718,876 A | 2/1998 | Rubino et al. | |
| 6,024,945 A | 2/2000 | Parekh | |
| 6,649,153 B1 | 11/2003 | Parekh et al. | |

FOREIGN PATENT DOCUMENTS

GB 1353915 5/1974

OTHER PUBLICATIONS

Quatrale, Richard P., et al., *The Mechanism of Antiperspirant Action by Aluminum Salts: The Effect of Cellophane Tape Stripping on Aluminum Salt–Inhibited Eccrine Sweat Glands*, Journal of the Society of Cosmetic Chemists, Mar.–Apr. 1981, 32:67–73.

Quatrale, Richard P., et al., *The Mechanism of Antiperspirant Action by Aluminum Salts: Histological Observations of Human Eccrine Sweat Glands Inhibited by Aluminum Chlorohydrate*, Journal of the Society of Cosmetic Chemists, May–Jun. 1981, 32:107–136.

Quatrale, Richard P., et al., *The Mechanism of Antiperspirant Action by Aluminum Salts: Histological Observations of Human Eccrine Sweat Glands Inhibited by Aluminum Zirconium Chlorohydrate Glycine Complex*, Journal of the Society of Cosmetic Chemists, Jul.–Aug. 1981, 32:195–221.

Quatrale, Richard P., et al., *The Site of Antiperspirant Action by Aluminum Salts in the Eccrine Sweat Glands of the Axilla*, Journal of the Society of Cosmetic Chemists, Nov.–Dec. 1985, 36:435–440.

*Primary Examiner*—Shelley A. Dodson
(74) *Attorney, Agent, or Firm*—Arthur J. Plantamura

(57) ABSTRACT

Disclosed are aqueous antiperspirant active compositions comprising an admixtures of basic aluminum halides and a metal cation salts which yield enhanced antiperspirant efficacy; and methods of making such antiperspirant compositions. The basic aluminum halides, optionally contain an amino acid or salts of amino acids, and/or antimicrobial agent and are combined with a metal cation antiperspirant (e.g., Ti salt or Hf salt or Sn salt or Zr salt) and optionally with a organic solvent having at least two carbon atoms and at least one hydroxy group and mixtures thereof and methods of making such mixtures. Basic aluminum halides having enhanced antiperspirant efficacy are produced by reacting (a) aluminum powder; (b) an aluminum halide; and (c) water at a temperature greater than about 85° C. This reaction is maintained until reaction products having an Al:halide ratio of about 1.2 to 1.5 and preferably 1.3 to 1.4:1; and a solution solids concentration of about 30–40 weight percent on an anhydrous basis are obtained. The basic aluminum halide of this invention are characterized as having a Size Exclusion Chromatography (HPLC) Test Band I of less than 5%, preferably less than 1%, Band II percent aluminum value of 20%–60% preferably about 35% to 55%, Band III percent aluminum value of 10% to 35% preferably 15%–30% and Band IV value of 15% to 50% preferably 25% to 35% and sum of peak 3 and 4 areas of at least 45% and no more than 70% and preferably 65%.

45 Claims, 1 Drawing Sheet

ENHANCED EFFICACY BASIC ALUMINUM HALIDES/METAL CATION SALT, ANTIPERSPIRANTS ACTIVES AND COMPOSITIONS CONTAINING SUCH MATERIALS AND METHODS FOR MAKING

BACKGROUND OF THE INVENTION

This invention relates to novel antiperspirant compounds comprising basic aluminum halides that have a particular molecular size distribution in admixture with a metal cation salt, e.g., salts of titanium, hafnium, tin or zirconium, preferable zirconium as well as the processes for their production and their use in antiperspirant composition. Basic aluminum halides, particularly chlorides, and their use as effective antiperspirant compounds are well known. Basic aluminum halides are complex structures made up of mixtures of polymeric and monomeric species of various sizes and molecular structures, depending upon their Al:Halide ratio, together with varying amounts of bound or coordinated water. The basic aluminum compounds are generally represented by the empirical formula:

$$Al_2(OH)_{(6-x)}Y_x \cdot nH_2O$$

wherein Y is Cl, Br or I and $0<x<6$ and n is about 0.8 to 4. It should be understood that the above formula is simplified because it is intended to include basic aluminum halides containing coordinated or bound molecules of water as well as basic aluminum halide polymer complexes and mixtures of the above.

Many attempts have been made to improve the antiperspirant efficacy and other properties of basic aluminum compounds, by altering its polymeric structure. The enhanced efficacy salts are typically differentiated from the conventional antiperspirant salts by reference to the various aluminum peaks that can be identified when the salt is analyzed by size exclusion chromatography typically HPLC (high pressure liquid chromatography). A suitable chromatographic technique is capable of resolving the Al in aluminum chlorohydroxide in at least four distinct peaks labeled peak 2 (which includes peaks 1 and 2), 3, 4 and 5. The retention time at which these peaks appear, their resolutions and their respective peak areas, are the function of the column (or columns) and mobil phase used. In general, enhanced efficacy salts have been described as having an increased peak 4 content, or an increased peak 4 to peak 3 ratio, compared to conventional (unactivated) salts. In several cases, enhanced efficacy salts have been described as having increased "Band III". It is important to note that generally, Bands I, II, III and IV of one system correspond respectively to peaks 1 and 2 (Band I), 3, 4 and 5 of the other system.

Related prior art is reviewed and discussed in the disclosure of our companion patent application Ser. No. 10/809, 996, filed on even date herewith. That disclosure is incorporated herein in its entirety.

As discussed in one of the patents alluded to in co-pending application, U.S. Pat. No. 5,718,876, basic aluminum halides and nitrates are prepared by reacting an aluminum powder, an aluminum halide or nitrate solution and water at a temperature greater than about 85° C. The reaction is maintained until reaction products having an Al:anion ratio of about 1.2 to about 1.8 and a solution solids concentration of about 28 to about 42 weight percent on an anhydrous basis are obtained. The reaction product is characterized as having a Size Exclusion Chromatography Test Band having a Band II percent aluminum value of at least about 50% and Band III percent aluminum value of less than 20%. Those products preferably also have a Band I percent aluminum value of less than about 1%. The method of that patent also encompasses the preparation of basic aluminum halide, nitrite and zirconium complexes. The zirconium compounds are preferably buffered with amino acid. The method of that patent for preparing these compounds comprises reacting, at room temperature, a basic aluminum halide and nitrate solution, with a zirconium compound or a zirconium/amino acid complex. The products obtained have a preponderance of aluminum species in Band II and the basic aluminum halide and zirconium complexes of these compounds provide improved efficacy when made into an antiperspirant composition using any of the usual vehicles of formulations known in the art.

SUMMARY OF THE INVENTION

Whereas, products obtainable according to the prior art, such as those disclosed in U.S. Pat. No. 5,718,876, are characterized as having a metals to chloride ratio between 1.2 to 1.8, a solution solids content of about 28% to about 42% anhydrous solids by weight percent, and have a size Exclusion Chromatography Test Band with a relative retention time corresponding to Band II of a Standard Basic Aluminum Chloride Size Exclusion Chromatogram, and a Band I percent aluminum value of less than 1%, a Band II percent value of greater than 50% and a Band III percent value of less than 20%, as distinguished therefrom, those of the present invention are characterized as having a metal to chloride ratio of between 1.2 to about 1.5 (vs. 1.2–1.8) preferably between 1.3 to 1.4 and a solution solids content maintained within a relatively narrow range of about 30% to about 40% (vs. 28–42%) anhydrous weight percent and Size Exclusion Chromatography Test Band with a Band I percent aluminum value of less than 5% (vs. less than 1%) a Band II value about 20–60% (vs. greater than 50%) a Band III value between about 10% and 35% (vs. less than 20%) and a Band IV value between 15 to 50% (vs. no mention of Band IV).

Accordingly, it is an object of the present invention to provide a novel enhanced efficacy basic aluminum halide admixed with at least one other antiperspirant active material selected from the group consisting of antiperspirant active of zirconium salts, basic zirconium carbonate, antiperspirant active of hafnium salts, antiperspirant active of titanium salts, antiperspirant active of tin salts and which can be produced economically.

It is another object of the present invention to provide such antiperspirants with substantially enhanced relative efficacy and to provide methods of forming such materials without the need for manufacturing steps previously thought to be necessary of heating diluted solutions of already manufactured basic aluminum halides at high temperatures and/or pressure conditions.

It is another object of the present invention to provide methods of forming enhanced efficacy aluminum zirconium antiperspirant solutions that have high concentrations thereby minimizing spray drying cost.

It is another object of this invention to provide a process for the preparation of an activated aluminum zirconium antiperspirant compositions, which have improved stability and do not require rapid drying after the desired solution is made which is a limitation applicable to most of the prior art enhanced efficacy products.

It is yet another object of the present invention to provide antiperpsirant compositions having enhanced antiperspirancy and are skin friendly.

In accordance with the discovery of the present invention, a careful control of the metals to anion ratio, maintenance of a suitably proper solution solids concentration and aging of the solution at room temperature, yields a product characterized as having a significantly more desirable size exclusion chromatography test band profile and superior efficacy.

The compositions according to the present invention may be prepared by simple mixing of the enhanced efficacy basic aluminum halide of this invention with a solution of a metal cation salt, for example, salts of titanium, hafnium, tin or zirconium. The temperature of such mixing can be at least room temperature or above room temperature of about 40° C.–100° C. or at reflux.

Preferred metal salts are those of zirconium compound selected from the group having a following general empirical formulas and with or without amino acid or salts of amino acids which are described in the hereto referred companion patent application Ser. No. 10/809,996.

$$ZrO(OH)_{2-nz}B_z$$

wherein z may vary from 0.9 to 2, and n is the valence of B and 2-nz is greater than or equal to 0 and B is selected from the group consisting of halides and nitrate. As an alternative to or in conjunction with the above described zirconium salts, it is also possible to employ zirconium basic carbonate which has been represented by empirical formulas [ZrO(OH)(CO$_3$)$_{0.5}$.nH$_2$O] or [Zr$_2$(OH)$_4$(CO$_3$)$_2$.nH$_2$O] which should not be interpreted as precise with respect to chemical structure but should be regarded only as a guide to molar ratio.

The zirconium compounds useful in the present invention include zirconyl chloride (also referred to as basic zirconium chloride or zirconium oxychloride), zirconyl hydroxy chloride, which may be represented by the formulas ZrOCl$_2$ and ZrO(OH)Cl, respectively and zirconium amino acid complex. These compounds are commercially available in solution form or may be prepared by dissolution of commercially available zirconium carbonate paste (carbonated hydrous zirconia) in the appropriate amount of the acid of the anion to be used, e.g., hydrochloric acid.

The zirconium compounds are preferably buffered with an appropriate amount of an amino acid. Appropriate amino acid buffers useful in the present method are, e.g., the salts of neutral amino acids, i.e., amino acids in which the number of amino groups is equal to the number of carboxyl groups in the molecule. Examples of such amino acids include glycine (including alkaline and alkaline earth glycinates and aluminum magnesium hydroxy glycinate compounds), DL-valine, -alaine, arginine, L-proline and mixtures thereof. The preferred amino acid for use in the present method is glycine.

The zirconium/amino acid complex may be prepared by refluxing a zirconium compound as described above with an appropriate amino acid for about 0.5 to about 4 hours and preferably about 1–2 hours, in order to form a reaction product. Once formed, this reaction product is mixed at room temperature with the basic aluminum halides prepared by the method as discussed in the companion patent application Ser No. 10/809,996. The reaction product is then dried to powder form by any appropriate means, however, spray drying is preferred. Other methods for producing the same or similar zirconium/amino acid complexes are disclosed in e.g., U.S. Pat. Nos. 4,017,599; 4,028,390; 4,223,010; 3,981,986 and British Patent 1,353,915, the disclosures of which are incorporated herein by reference.

It is to be understood, however, that hafnium and mixtures of hafnium and zirconium can be substituted for zirconium without departing from the scope and spirit of this invention. Commercial sources of zirconium usually contain about 2 to 5% of hafnium. Heretofore and hereinafter in this specification the antiperspirant complexes of this invention will be referred to as aluminum-zirconium complexes even though a complex may contain 2–5% of hafnium.

Other antiperspirant active salts which may be selected from the group consisting of hafnium salts, titanium salts, tin salts, and mixtures thereof.

DETAILED DESCRIPTION OF THE INVENTION

Figure 1:
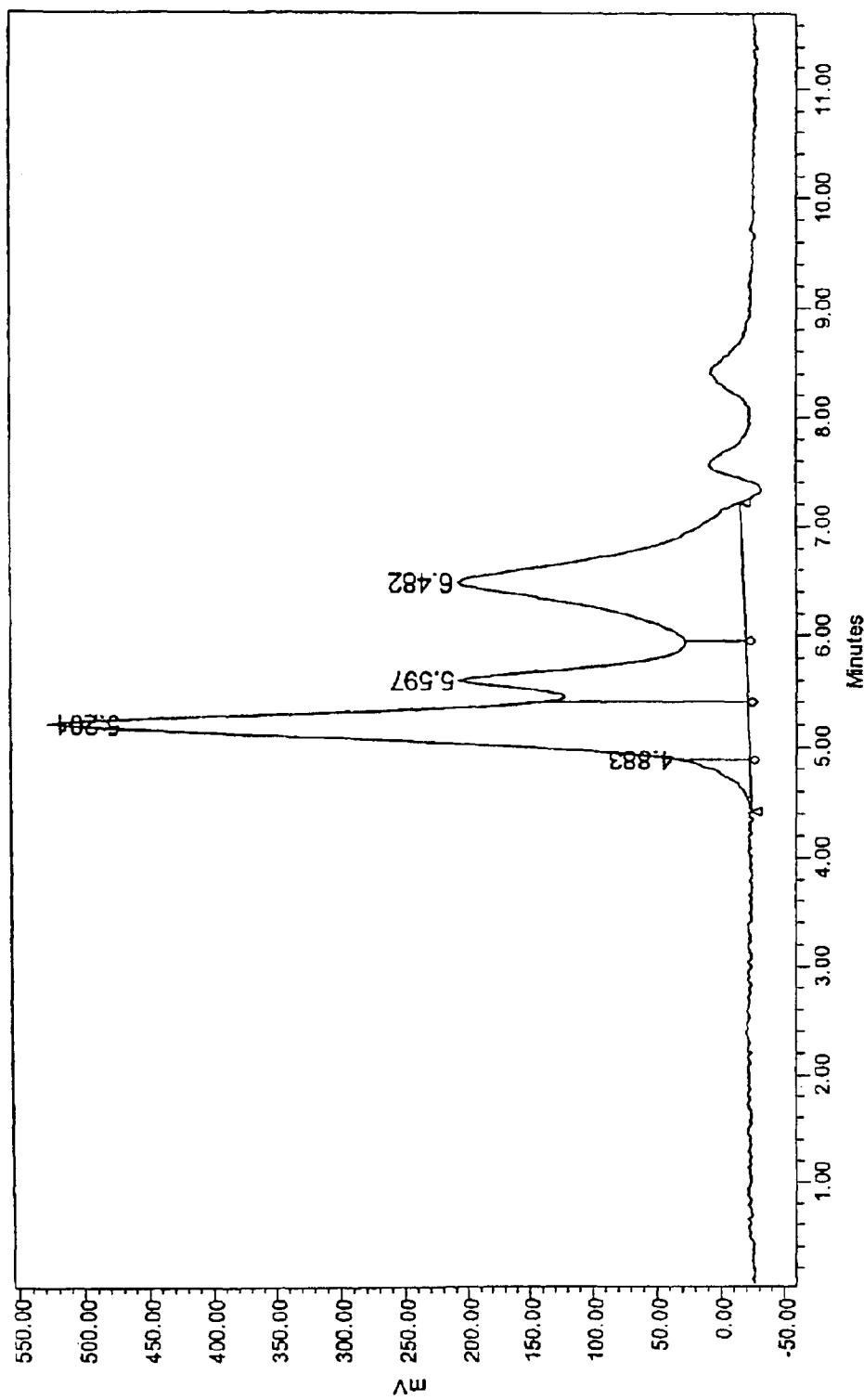
FIG. 1 is a typical chromatograph of basic aluminum chloride powder.

The term "enhanced efficacy antiperspirant active" is used interchangeably herein with the terms "activated antiperspirant active" or "improved efficacy antiperspirant" active. The enhanced antiperspirant contemplated herein means any aluminum containing antiperspirant material whose polymeric form is measurably shifted to lower molecular weight polymers relative to the polymer distribution of a typical aluminum chlorohydroxide (5/6 basic aluminum chloride). The measurable shift is determined by high-pressure liquid chromatography as described herein. In the analyses each sample is dissolved in deionized water to form about 5 mg/ml aluminum solution and filtered through a 0.45μ filter and chromatographed within 5 minutes using 10 microliter samples at a flow rate of 0.7 ml/min at a pressure of 450–500 psig and 0.01N HNO3 eluent. Two chromatographic columns used in series are a Waters Porasil column 30 cm long with an ID of 3.9 mm, a pore size of 125° A, particle size of 10μ and a Phenomenex Column 25 cm long with an ID of 4.6 mm, a pore size of 60° A and particle size of 10μ. A Waters 2414 Differential Refractometer was used to scan chromatograph. Relative peak areas, and peak heights were calculated using Waters Millenium$^{32}$ Chromatography Manager.

The peaks observed in the chromatogram are designated in order of appearance on the chromatograms as peaks 1–2, (appears as a single peak, Band I) and peak 3 (Band II), peak 4 (Band III) and peak 5 (Band IV). (See FIG. 1) The area of the peaks correspond to the relative concentration of aluminum polymer species exiting the column during the specified time passed from the injected sample.

The term "metal/chloride ratio" is used interchangeably herein with metal/halide ratio or metal/anion ratio and metals refer to (Al+Zr) or (Al+Zr+Hf), etc. the ratio always refers to atomic ratio.

The antiperspirant active compositions contemplated by the invention:

(a) basic aluminum halides having the empirical formula $$Al_2(OH)_{6-x1}Y_{x1}Rp\ (AA)q$$

wherein Y is Cl, Br, or I and $1.3 \leq x_1 \leq 1.7$, wherein R is an organic solvent having at least two carbon atoms and at least one hydroxy group and p has a value of $0 \leq p \leq 1.0$ and wherein (AA) is amino acid or amino acid compound and $0 \leq q \leq 0.5$ and aluminum material being further characterized by:

(i) size exclusion high performance liquid chromatography test band having a Band I relative area value of less than 5%, a Band II relative area value of 20% to 60%, Band III relative area value of 10% to 35% and Band IV relative area value of 15% to 50% and the sum of Band III and Band IV relative area value of at least 45% and no more than 70% and (ii) $^{27}$Al NMR spectrum wherein at least 45% of the total area under the spectrum from +100 ppm to −100 ppm is contained in the sum of the areas of resonance lines at or below 10 ppm and (iii) in which the area of the resonance at 63 ppm is less than 0.1% of the total area under the spectrum from +100 ppm to −100 ppm and (iv) which comprises 30 to 42% by weight of anhydrous basic aluminum halide antiperspirant active in water in admixture with (b) at least one other antiperspirant active material which is selected from the group consisting of antiperspirant active of salts, of metals selected from the group consisting of titanium, hafnium, tin and zirconium.

The antiperspirant prepared in accordance with the present method are characterized as having metal to anion or halide ratio between 0.9:1 to about 1.7:1, and solution solids content maintained within a relatively narrow range of about 30 to 40 anhydrous weight percent.

For the basic aluminum halide (a) of this invention the method comprises reacting (i) aluminum powder (ii) an aluminum halide solution and (iii) water. Examples of the aluminum powder are such as Ampal grade 601, Alcoa grade 101 and Alcan grade 52R.

In general, any standard aluminum halide conventionally used in the art may be used in the present method. Such solutions generally have a solution solids concentration of about 28 weight percent. This corresponds to an aluminum content of about 5.7%. However, it will be evident to one skilled in the art that aluminum halide solutions having other concentrations may also be used in the present method.

The three components employed in the method of the present invention, i.e., the aluminum powder, the aluminum halide and water, should be reacted at a temperature greater than about 85° C. Preferably, the components are reacted at a temperature of about 91° C. to about 95° C.

The reaction is maintained until a desired reaction product having an Al:halide ratio of about 1.2 to about 1.5 and a solution solids concentration of about 30 to about 40 anhydrous weight percent is obtained. When the desired reaction product is obtained, the reaction product is cooled, filtered and aged at room temperature until the desired HPLC is obtained.

The basic aluminum halides of the present invention may also be prepared by an "indirect process" which comprises taking a conventional basic aluminum halide solution having a suitable Al:halide ratio that is adjusted to an Al:halide ratio of the solution to about 1.2:1 to 1.5:1, preferably 1.3:1 to 1.4:1, by adding an appropriate either aged or unaged lower basicity aluminum halide solution or HX or AlX$_3$.6H$_2$O, where X can be Cl, Br or I solutions thereto. This adjusted composition may be heated to 95° C.–100° C. for a period that may range from about 10 minutes to about 6 hours and may be aged at room temperature until the desired chromatographic distribution of aluminum species is obtained, i.e., until the products of this process comprise the desired Band I, II, III, and IV percentages.

The preferred metal cation compounds admixed with the basic aluminum halides are those encompassed within the formula:

ZrO(OH)$_{2-nz}$B$_z$ wherein z may vary from 0.9 to 2, and n is the valence of B and 2−nz is greater than or equal to 0 and B is selected from the group consisting of halides and nitrate added at room temperature, 50° C.–100° C., or at reflux. As an alternative to or in conjunction with the above described zirconium salts, it is also possible to employ zirconium basic carbonate which has been represented by empirical formulas [ZrO(OH)(CO$_3$)$_{0.5}$.nH$_2$O] or [Zr$_2$(OH)$_4$(CO$_3$)$_2$.nH$_2$O] which should not be interpreted as precise with respect to chemical structure but should be regarded only as a guide to molar ratio.

The addition of amino acid or amino acid salts and the quantity thereof depends on the desired Al/Zr ratio and the pre-existing presence of amino acid or amino acid salts in the zirconium salt solution or in the basic aluminum halide.

The irritancy potential of the products derived by the present invention can be further reduced by buffering basic aluminum halides with amino acids or compounds of amino acids. In addition to amino acids per se, such as glycine, amino acid compounds that are useful herein include alkali metal and alkaline earth metal salt of amino acids as well as ammonium or hydroxy salts of amino acids.

As used herein, the term "alkaline" as applied to salts of amino acids, is not intended to be limited to those having a pH greater than 7.0, since some complex or imperfectly neutralized salts can have a pH less than 7.0 and still be useful in this invention. Instead, alkaline is meant to refer to the usual alkali and alkaline earth metal cations, including ammonium and hydroxy cations.

Among the salts of amino acids useful herein are those derived from amino acids in which the number of amino groups is equal to the number of carboxyl groups in the molecule. Examples of such amino acids include glycine, DL-valine, alanine, lysine, arginine, and L(−) prolinates. Suitable salts of other amino acids that may be used in the present invention will be evident to those skilled in the art.

Suitable hydroxy salts of amino acids useful herein include the monohydroxy and dihydroxy aluminum salts of amino acids, and aluminum-magnesium-hydroxy-glycine compounds, such as monohydroxy aluminum glycinate, magnesium glycinate and calcium glycinate. These hydroxy salts are the reaction products of aluminum hydroxy antacids and the desired amino salt. Since these glycinates are available in different basicities, the amount of glycinate or other salt to be used depends upon the particular basicity of the amino salt. In general, about 0.5% to 10% by weight of the above salts can be used with the products of this invention. The desirable method is to add the amino acid or the salt of an amino acid or a combination thereof to the basic aluminum halide solution having the desired chromatographic distribution and spray drying the buffered solution.

Other compounds that may be usefully employed in reducing acidity and irritancy potential are disclosed in U.S. Pat. No. 6,024,945 of Parekh which is incorporated here in its entirety by reference.

It is desirable for an antiperspirant product to provide aesthetics (pleasing skin feel) in addition to excellent antiperspirancy. It is also desirable that the basic aluminum halides of this invention have an improved solubility for certain formulation without sacrificing antiperspirant efficacy. This can be achieved by adding a suitable organic solvent such as propylene glycol or polyethylene glycol to the desired basic aluminum halide of this invention and the solution may be heated at about 85° C.–95° C. for about one hour. Also, if the modifying component is a polyhydric alcohol, preferably glycerin, it provides excellent skin conditioning and moisturizing without adversely affecting efficacy of the antiperspirants. Other compounds which can provide skin friendly antiperspirants without sacrificing efficacy are listed in U.S. Pat. No. 6,649,153 B1 the disclosure of which is incorporated here by reference.

It will be understood in the preparation of the activated mixed aluminum/metal cation antiperspirant salt, preferably Al/Zr, antiperspirant of the present invention that the testing of the basic aluminum halide utilized in the aforementioned companion pending application Ser. No. 10/809,996, is applicable in the disclosure of the present application. The distinction characterizing the present application resides in admixing the basic aluminum antiperspirant active prepared in accordance with that companion application with the metal cation salt active compound of the present invention.

The product of this invention possesses superior antiperspirancy and is more economical to produce. Since the metal salts are more acidic than the skin surface, sweat or plasma, it is inevitable that neutralization will occur to a varying degree depending on the depth of penetration into the skin or down the sweat duct. Ductal diffusion is a function of molecular weight and charge. Thus, lower molecular weight aluminum species of this invention are more likely to give plug deeper down the eccrine gland as has been demonstrated by Quatrale, et al., (The Mechanism of Antiperspirant Action by Aluminum Salts) and in the reference on the effect of cellophane tape stripping on aluminum salt inhibited eccrine sweat glands. (Journal of the Society of Cosmetic Chemists. 32: 67–73 1981; 32: 107–136; 32: 195–221 and 36: 435–440). The relevant disclosures of these articles are incorporated by reference.

The invention is further described by reference to the following illustrate examples details of which, except as recited in the appended claims are not to be construed as limitations.

EXAMPLE 1

Basic aluminum halide of this invention was prepared according to the procedure outlined in the co-pending application. Chemical analysis and HPLC results of the solution were Al=11.5% Cl=10.8% Al:Cl ratio 1.40 and HPLC peak areas where for Band I 0.78%, Band II 56.46%, Band III 12.75% and Band IV 30.01%. 12,500 gms of this basic aluminum chloride solution was mixed with 815 gms of glycine and dissolved and to this 6000 gms of zirconium hydroxy chloride solution having chemical analysis of Zr=24%, Cl=10.02% and Cl/Zr ratio of 1.095 and 5500 gms of water were added. 225 gms of additional glycine was added to the 10 kg of solution and the solution was aged at room temperature for about 48 hours. The final solution with anhydrous solids content of 30.1% was divided into two parts and one part was spray dried using a two fluid nozzle atomizer at an inlet temperature of about 500° F.–600° F. and outlet temperature of about 240° F.–245° F.

The resultant aluminum zirconium tetrachlorohydrex spray dried powder's chemical analysis and HPLC results were as follows: Al=13.94%, Zr=14.10%, Cl=18.59%, glycine=12.5%, Al/Zr ratio of 3.41, metals/chloride ratio of 1.27, anhydrous solids content of 74.4%, Band I 9.58%, Band II 46.96%, Band III 13.19% and Band IV 30.27%. Band III/II peak area ratio was 0.281.

EXAMPLE 2

Aluminum zirconium tetrachlorohydrex glycine solution of Example 1 was refluxed for 2 hrs. and then was spray dried using two fluid nozzle atomizer at an inlet temperature of about 500° F.–600° F. and outlet temperature of about 240° F.–245° F. The resultant aluminum zirconium tetrachlorohydrex glycine complex powder's chemical analysis and HPLC results were as follows: Al=13.72%, Zr=13.9%, Cl=18.31%, glycine=12.31%, Al/Zr ratio 3.4, M/Cl ratio 1.27, anhydrous solids=73.3%, Band I 17.75%, Band II 38.96%, Band III 12.12%, Band IV 31.18%. Band III/II peak area ratio was 0.31.

It will be apparent from the foregoing that various equivalents and substitutions may be applied by those skilled in the art and such are contemplated as being within the scope of the invention, except to the extent that such equivalents or substitutions are specifically excluded, by the express language of the appended claims.

What is claimed is:

1. An aqueous antiperspirant active composition comprising admixing:

(a) a basic aluminum halide having the empirical formula $$Al_2(OH)_{6-x1}Y_{x1}Rp(AA)q$$

wherein Y is Cl, Br, or I and $1.3 \leq x_1 \leq 1.7$, wherein R is an organic solvent having at least two carbon atoms and at least one hydroxy group and p has a value of $0 \leq p \leq 1.0$ and wherein (AA) is amino acid or amino acid compound and $0 \leq q \leq 0.5$ and aluminum material being further characterized by:

(i) size exclusion high performance liquid chromatography test band having a Band I relative area value of less than 5%, a Band II relative area value of 20% to 60%, Band III relative area value of 10% to 35% and Band IV relative area value of 15% to 50% and the sum of Band III and Band IV relative area value of at least 45% and no more than 70% and (ii) $^{27}$Al NMR spectrum wherein at least 45% of the total area under the spectrum from +100 ppm to −100 ppm is contained in the sum of the areas of resonance lines at or below 10 ppm and (iii) in which the area of the resonance at 63 ppm is less than 0.1% of the total area under the spectrum from +100 ppm to −100 ppm and (iv) which comprises 30 to 42% by weight of anhydrous basic aluminum halide antiperspirant active in water and (b) at least one other antiperspirant active material which is selected from the group consisting of antiperspirant active of Zr salts, antiperspirant active of Hf salts, antiperspirant active of Ti salts and antiperspirant active of Sn salts.

2. The antiperspirant composition of claim 1 wherein nonaluminum antiperspirant compound is selected from;

a) the compounds having a following general empirical formula:

$$ZrO(OH)_{2-nz}B_z$$

wherein z may vary from 0.9 to 2, and n is the valence of B and 2-nz is greater than or equal to 0 and B is selected from the group consisting of halides and nitrate and with or without amino acid or salts of amino acids; and b) zirconium basic carbonate compounds represented by empirical formulas $$[ZrO(OH)(CO_3)_{0.5} \cdot nH_2O] \text{ or } [Zr_2(OH)_4(CO_3)_2 \cdot nH_2O].$$

3. The antiperspirant composition of claim 1 wherein the amino acids can be glycine, DL-valine, alanine, arginine, lysine, and salts of amino acids can be sodium glycinate, calcium glycinate, magnesium glycinate, strontium glycinate and mixtures thereof.

4. The antiperspirant composition of claim 2 wherein the amino acids can be glycine, DL-valine, alanine, arginine, lysine, and salts of amino acids can be sodium glycinate, calcium glycinate, magnesium glycinate, strontium glycinate and mixtures thereof.

5. The antiperspirant composition of claim 2 wherein aluminum to zirconium molar ratio is from 1:10 to 10:1 and wherein the metal/halide molar ratio is 0.9:1 to 1.7:1.

6. The antiperspirant solution of claim 1 formed by mixing in an aqueous solution natural or synthetic antimicrobial compound.

7. The antiperspirant of claim 6 wherein the antimicrobial is selected from triclosan, triclocarbon, zinc compounds, green tea extract, Neem oil and mixtures thereof.

8. The antiperspirant solution of claim 1 where Y is chloride and Al:Cl molar ratio is 1.3:1 to 1.4 to 1.

9. The antiperspirant solution of claim 1 where Y is chloride and Al:Cl molar ratio is 1.2:1 to 1.5:1.

10. The antiperspirant solution of claim 1 where an amino acid is glycine.

11. The antiperspirant solution of claim 2 where an amino acid is glycine.

12. The antiperspirant solution of claim 2 containing an amino acid compound and wherein the amino acid compound is selected from an alkali metal, an alkaline earth metal, ammonium or hydroxy salt of an amino acid, a metal glycinate and a hydroxy aluminum salt of an amino acid.

13. The antiperspirant solution of claim 2 where amino acid compound is an alkali metal, an alkaline earth metal, ammonium or hydroxy salt of an aminoacid, a metal glycinate and a hydroxy aluminum salt of an amino acid.

14. The antiperspirant composition of claim 2 where amino acid salt is selected from sodium glycinate, magnesium glycinate, potassium glycinate, calcium glycinate, zinc glycinate and strontium glycinate and mixtures thereof.

15. The antiperspirant solution of claim 1 where the organic solvent is a polyhydric alcohol having at least three to about 12 carbon atoms and at least two hydroxy groups and is present at a concentration of about 1 to 10 weight percent.

16. The antiperspirant solution of claim 2 where the organic solvent is a polyhydric alcohol having at least three to about 12 carbon atoms and at least two hydroxy groups and is present at a concentration of about 1 to 10 weight percent.

17. The antiperspirant solution of claim 1 wherein the organic solvent is a polyhydric alcohol and is selected from glycerin, diglycerol, glyceridacid and mixtures thereof.

18. The antiperspirant solution of claim 2 wherein the organic solvent is a polyhydric alcohol and is selected from glycerin, diglycerol, glyceridacid and mixtures thereof.

19. The antiperspirant solution of claim 1 wherein the organic solvent is selected from the group consisting of ethylene glycol, polyethylene glycols, propylene glycol, dipropylene glycol, sorbitol, diethylene glycol, butylene glycol, hexylene glycol, 1,2-propylene glycol, 1,3 propylene glycol, glycerin, 1,2-hexanediol, hexanetriol, tripropylene glycol, propylene glycol methyl ether, isopropyl glycerol ether, dipropylene glycol methyl ether and combinations thereof at a concentration of about 1 to 10 weight percent.

20. The antiperspirant solution of claim 2 wherein the organic solvent is selected from the group consisting of ethylene glycol, polyethylene glycols, propylene glycol, dipropylene glycol, sorbitol, diethylene glycol, butylene glycol hexylene glycol, 1,2-propylene glycol, 1,3 propylene glycol, glycerin, 1,2-hexanediol, hexanetriol, tripropylene glycol, propylene glycol methyl ether, isopropyl glycerol ether, dipropylene glycol methyl ether and combinations thereof at a concentration of about 1 to 10 weight percent.

21. The antiperspirant powder obtained by spray drying the solution of claim 1.

22. The antiperspirant powder obtained by spray drying the solution of claim 2.

23. The antiperspirant powder obtained by spray drying the solution of claim 6.

24. The antiperspirant powder of claim 21 which have an average particle size of about 15 to 30 microns.

25. The antiperspirant powder of claim 22 which have an average particle size of about 15 to 30 microns.

26. The antiperspirant powder of claim 23 which have an average particle size of about 15 to 30 microns.

27. The antiperspirant powder of claim 22 which has bulk density from about 0.5 gm/cc to 2 gm/cc.

28. The antiperspirant powder of claim 22 which is micronized to have an average particle size of about 1 to 15 microns.

29. A method of preparing an antiperspirant active solution comprising an admixture of:

A material having the empirical formula $$Al_2(OH)_{6-x1}Y_{x1}Rp(AA)q$$

wherein Y is Cl, Br, or I and $1.3 \leq x_1 \leq 1.7$, wherein R is an organic solvent having at least two carbon atoms and at least one hydroxy group and p has a value of $0 \leq p \leq 1.0$ and wherein (AA) is amino acid or amino acid compound and $0 \leq q \leq 0.5$ and aluminum material and having:

(i) a size exclusion high performance liquid chromatography test band having a Band I relative area value of less than 5%, a Band II relative area value of 20% to 60%, Band III relative area value of 10% to 35% and Band IV relative area value of 15% to 50% and the sum of Band III and Band IV relative area value of at least 45% and no more than 70%;

(ii) an $^{27}$Al NMR spectrum wherein at least 45% of the total area under the spectrum from +100 ppm to –100 ppm is contained in the sum of the areas of resonance lines at or below 10 ppm and (iii) in which the area of the resonance at 63 ppm is less than 0.1% of the total area under the spectrum from +100 ppm to –100 ppm and at least one other antiperspirant active metal cation material selected from the group consisting of antiperspirant active of Zr salts, antiperspirant active of Hf salts, antiperspirant active of Ti salts and antiperspirant active of Sn salts comprising the steps of:

(a) making basic aluminum halide by reacting aluminum powder, aluminum halide and water at a temperature greater than 85° C. but below the reflux temperature;

(b) maintaining this reaction until the reaction products having Al:halide ratio of 1.2 to 1.5 and solution solids concentration of about 30 to 42 weight percent on an anhydrous basis;

(c) cooling said reaction products to about room temperature;

(d) filtering and aging said reaction products at about room temperature from about 1 day to 6 months until the desired size exclusion chromatograph is obtained; and (e) admixing said reaction products with an amino acid or amino acid compound and with said metal cation material.

30. The method of claim 29 in which the basic aluminum halide is obtained by taking a conventional basic aluminum halide solution having a suitable aluminum to halide ratio adjustable to an Al:halide ratio of the solution to about 1.2:1 to 1.5:1 and adding an appropriate amount of aged or unaged lower basicity aluminum halide solution or HX or $AlX_3.6H_2O$ solution thereof, wherein X can be Cl, Br or I, and heating the aluminum halide to about 50° C.–100° C. for a period of about 10 minutes to about 6 hours and thereafter aging the resulting aluminum halide at room temperature until the desired chromatographic distribution of aluminum species is obtained.

31. A method of claim 29 comprising the steps of making the basic aluminum halide; mixing a zirconium salt selected from those having the general formula:

$$ZrO(OH)_{2-nz}B_z$$

wherein z may be from 0.9 to 2 and n is the valence of B and 2−nz is greater than or equal to a 0 and B is selected from the group consisting of halides and nitrate at a mixing temperature ranging from room temperature and including reflux temperature to 100° C.

32. The method of claim 29 wherein a zirconium basic carbonate which has been represented by empirical formulas $[ZrO(OH)CO_{3\ 0.5}.nH_2O]$ or $[Zr_2(OH)_4(CO_3)_2.nH_2O]$ as admixed with said basic aluminum halide.

33. The method of claim 29 wherein the said method includes the addition of an organic solvent before, during or after aging.

34. The method of claim 30 wherein the said method includes the addition of an organic solvent before, during or after aging.

35. The method of claim 31 wherein the said method includes the addition of an organic solvent before, during or after the admixing of a zirconium salt with basic aluminum halide of invention.

36. The method of claim 29 wherein the basic aluminum halide antiperspirant active is first buffered with an amino acid and or a salt of amino acids followed by the addition of an organic solvent.

37. The method of claim 30 wherein the desired basic aluminum halide antiperspirant active is first buffered with an amino acid and or a salt of amino acids followed by the addition of an organic solvent.

38. The method of claim 31 wherein the desired basic aluminum halide antiperspirant active is first buffered with amino acid and or a salt of amino acids followed by the addition of an organic solvent.

39. The method of claim 31 wherein the reaction product obtained is spray dried to powder.

40. The method of claim 39 wherein the said method further comprises micronizing or screening or air classification or combination thereof to achieve the desired particle size distribution, particle shape distribution and density.

41. A method of spray drying basic aluminum halides and compositions as in claim 39 wherein the atomizer used is csc disc or two fluid nozzle or single fluid nozzle or multiple drilled hole disc or porous metal disc.

42. A method of claim 31 wherein the reaction product is dried using any known suitable conventional industrial method.

43. A method making aluminum zirconium antiperspirant as in claim 39 wherein the dried powder has a loss on drying when kept at 105° C. for 2 hrs. from 5% to 20% by weight.

44. A method of making aluminum zirconium antiperspirant in claim 40 wherein the particles comprising thin walled or thick walled hollow spheres, solid spheres and irregular shaped non-hollow particles in an admixture suitable to achieve the desired particle size and shape distribution.

45. A method of making aluminum zirconium antiperspirant as in claim 43 wherein the critical humidity of the product is about 5%–20%.

* * * * *

UNITED STATES PATENT AND TRADEMARK OFFICE
CERTIFICATE OF CORRECTION

| | |
|---|---|
| PATENT NO. | : 7,014,843 B2 |
| APPLICATION NO. | : 10/807872 |
| DATED | : March 21, 2006 |
| INVENTOR(S) | : Parekh et al. |

It is certified that error appears in the above-identified patent and that said Letters Patent is hereby corrected as shown below:

<u>Column 1</u>

Line 54, please change 10/809,996 to -- 10/807,996 --

<u>Column 3</u>

Line 18, please change 10/809,996 to -- 10/807,996 --
Line 59, please change 10/809,996 to -- 10/807,996 --

<u>Column 4</u>

Line 34, please change 125° A to -- 125°A --
Line 36, please change 60° A to -- 60°A --

<u>Column 7</u>

Line 8, please change 10/809,996 to -- 10/807,996 --

Signed and Sealed this

Twenty-ninth Day of August, 2006

JON W. DUDAS
*Director of the United States Patent and Trademark Office*